United States Patent
Jiang et al.

(10) Patent No.: US 12,017,981 B2
(45) Date of Patent: Jun. 25, 2024

(54) METHOD FOR PREPARING ACETALDEHYDE FROM ACETYLENE UNDER CATALYSIS OF ZAPO MOLECULAR SIEVE

(71) Applicant: BOZUN INVESTMENT GROUP LIMITED, Beijing (CN)

(72) Inventors: Yibo Jiang, Beijing (CN); Yufan Ying, Beijing (CN); Zheng Li, Beijing (CN)

(73) Assignee: BOZUN INVESTMENT GROUP LIMITED, Beijing (CN)

( * ) Notice: Subject to any disclaimer, the term of this patent is extended or adjusted under 35 U.S.C. 154(b) by 39 days.

(21) Appl. No.: 17/635,515

(22) PCT Filed: Apr. 28, 2021

(86) PCT No.: PCT/CN2021/090604
§ 371 (c)(1),
(2) Date: Feb. 15, 2022

(87) PCT Pub. No.: WO2021/227875
PCT Pub. Date: Nov. 18, 2021

(65) Prior Publication Data
US 2023/0059377 A1    Feb. 23, 2023

(30) Foreign Application Priority Data
May 11, 2020 (CN) .......................... 202010391362.3

(51) Int. Cl.
C07C 45/26 (2006.01)
C07C 45/78 (2006.01)
(52) U.S. Cl.
CPC .............. C07C 45/26 (2013.01); C07C 45/78 (2013.01)
(58) Field of Classification Search
CPC ...... C07C 45/26; C07C 45/78; C07C 2529/84
See application file for complete search history.

(56) References Cited

U.S. PATENT DOCUMENTS

| 3,189,556 A | * | 6/1965 | Dille | ......................... B01J 23/80 502/170 |
| 3,291,839 A | * | 12/1966 | Carney et al. | .......... C07C 45/26 568/467 |
| 2005/0143597 A1 | * | 6/2005 | Mizushima | .......... B01J 31/1875 562/544 |

FOREIGN PATENT DOCUMENTS

| CH | 644834 A5 | 8/1984 |
| CN | 1592727 A | 3/2005 |
| CN | 102219660 A | 10/2011 |
| CN | 103113201 A | 5/2013 |
| CN | 108311174 A | 7/2018 |
| CN | 108993576 A | 12/2018 |
| CN | 111574344 A | 8/2020 |
| GB | 393690 | 6/1933 |

OTHER PUBLICATIONS

Chinese Office Action dated Feb. 14, 2023 issued in Chinese Patent Application No. 202010391362.3.
Second Chinese Office Action dated Jul. 11, 2023 issued in Chinese Patent Application No. 202010391362.3, pp. 1-5.
"Basic Organic Synthesis Process", Editor, Zhangreng Wu, pp. 1-6, 198 (1982) (English translation).
Amoy Glacial Acetic-Acid Factory et al., "Catalysis by Coordination Activation, II. Vapor-Phase Catalytic Hydration of Acetylene with a Type of Zinc-Compound Catalyst", Acta Chimica Sinica, vol. 33(2), pp. 113-124, English Abstract (1975).
Chemical production process diagram, Chemical Industry Press, pp. 1-14, 248-251 (1997) (English translation).
Shouzhen, C. et al., "Study of Metal Aluminophosphate Molecular Sieve Catalyst-(II)ZAPO-5 ' Catalyst", Journal of Fujian Normal University (Natural Science), vol. 7(1), pp. 45-49, (1991) (English Abstract).
"Teaching and Research Group of Basic Organic Synthesis", Lanzhou Chemical Engineering School "Process Flow for Acetylene in Liquid-Phase Hydration", Fundamentals of Organic Synthesis Technology, Aug. 31, 1962, vol. 2, pp. 43-47.
Chen, S., et al., "Study of Metal, Aluminophosphate Molecular Sieve Catalyst-(II) ZAPO-5' Catalyst", Journal of Fujian Normal University (Natural Science Edition), Feb. 28, 1991, No. 1, pp. 45-49 (English Abstract attached).
PCT International Search Report from the China National Intellectual Property Administration, dated Jul. 28, 2021, for PCT/CN2021/090604, pp. 1-5.

* cited by examiner

*Primary Examiner* — Sikarl A Witherspoon
(74) *Attorney, Agent, or Firm* — McDonnell Boehnen Hulbert & Berghoff LLP

(57) ABSTRACT

Disclosed is a method for preparing acetaldehyde from acetylene under the catalysis of a ZAPO molecular sieve. The method comprises the steps of pre-heating an acetylene raw material gas and water, subjecting same to continuous hydration in a fluidized bed under the catalysis of the ZAPO molecular sieve to prepare acetaldehyde, and then subjecting same to separation, absorption and rectification to obtain an acetaldehyde product, wherein the catalyst can be continuously regenerated for use. The process of the present application is simple, stable and efficient, solves the problem of the dependence nature of the production of acetaldehyde by means of acetylene hydration on a mercury catalyst, avoids the harm caused by mercury to the human body and the environment, and has higher production and use values.

15 Claims, 1 Drawing Sheet

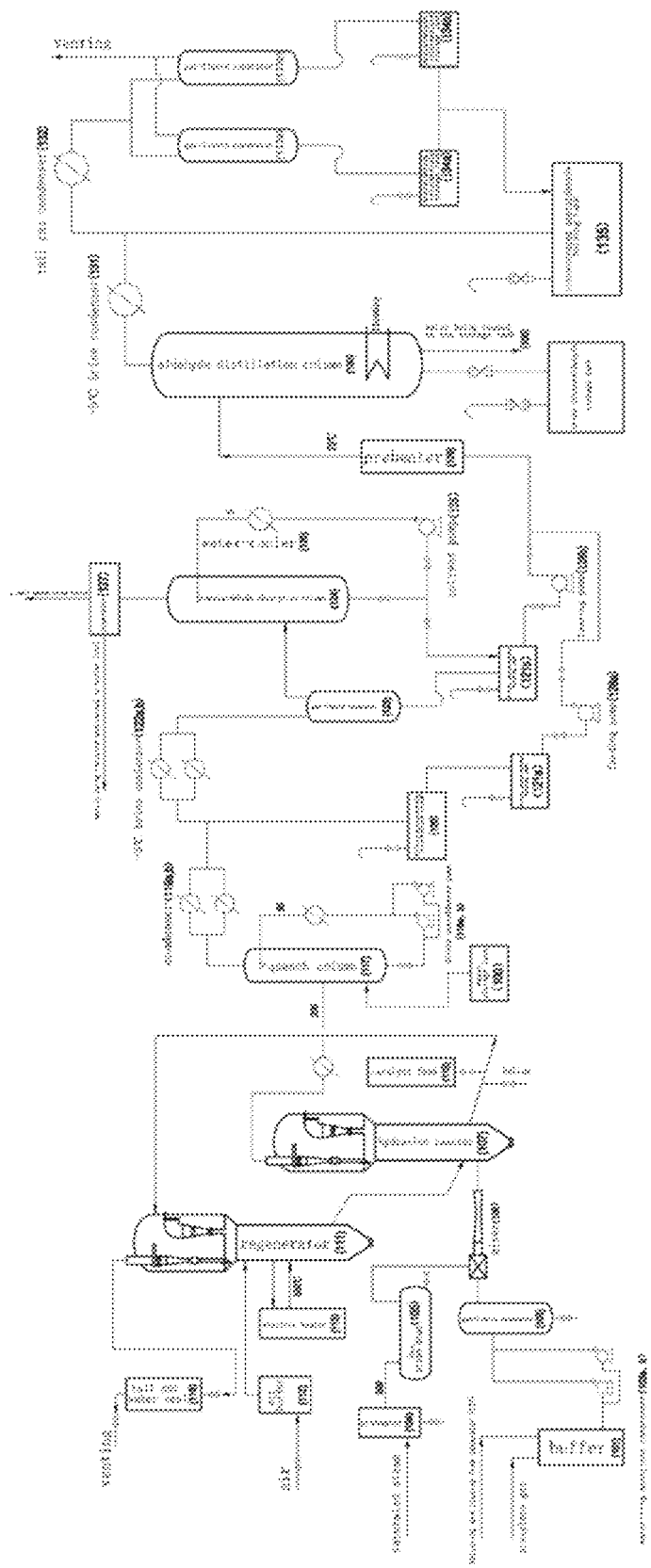

METHOD FOR PREPARING ACETALDEHYDE FROM ACETYLENE UNDER CATALYSIS OF ZAPO MOLECULAR SIEVE

CROSS-REFERENCE

This application is a 371 U.S. national phase of PCT/CN2021/090604, filed Apr. 28, 2021, which claims priority from ON patent application serial no. 202010391362.3, filed May 11, 2020, both which are incorporated by reference in its entirety.

FIELD OF THE INVENTION

The application belongs to the field of chemical technology, and specifically relates to a preparation method for producing acetaldehyde by catalyzing acetylene with ZAPO molecular sieve.

BACKGROUND OF THE INVENTION

Acetaldehyde, also known as acetic aldehyde, belongs to aldehydes and is an organic compound with the molecular formula of $CH_3CHO$ or MeCHO. Acetaldehyde is regarded as one of the most important compounds among aldehydes due to its widespread presence in nature and large-scale industrial production, Acetaldehyde can be found in coffee, bread, and ripe fruits. It can also be produced as a metabolite via plants. Ethanol is oxidized into acetaldehyde, which is considered as the cause of hangover. Acetaldehyde is liquid at room temperature, colorless, flammable, and has a pungent odor. Its melting point is −123.5° and its boiling point is 20.2° C. Acetaldehyde can be reduced to ethanol or can be oxidized to acetic acid.

Acetaldehyde is an important basic organic chemical raw material that can be used for the production of acetic acid: acetic anhydride, ethyl acetate, butyraldehyde, butanol, pentaerythritol, pyridine and chloroacetaldehyde, etc. At present, there are mainly four methods for industrial production of acetaldehyde: (1) ethanol dehydrogenation or oxidation method; (2) light oil oxidation method; (3) ethylene direct oxidation method; (4) acetylene hydration method.

In recent years, due to the energy structure characterized by rich coal and less oil in China, the coal chemical industry has developed rapidly, and producing acetaldehyde by acetylene hydration has gradually become an advantageous process route. At present, the mainstream method for preparing acetaldehyde on the market also adopts the method of acetylene hydration production. In addition, in the traditional mercury-catalyzed acetylene hydration process for producing acetaldehyde, the mercury catalyst may cause serious harm to the human body and the environment, and the processing efficiency is relatively average.

SUMMARY OF THE INVENTION

In this regard, the present application proposes a new production process for preparing acetaldehyde by acetylene hydration and a catalyst system thereof, and the catalyst system does not contain mercury, so as to solve the problem that the conventional preparation methods of acetaldehyde on the market currently have ordinary efficiency and are more harmful to the environment.

In order to solve the above problems, the present application provides a preparation method for continuously producing acetaldehyde by catalyzing the gas phase hydration of acetylene with ZAPO molecular sieve. With reference to the drawings, the method specifically comprises the following steps:

(1) Preheating and mixing materials: acetylene enters a buffer from a gas tank, and is pressurized by a water-ring acetylene compressor before entering a gas-liquid separator (103) to remove moisture therein, and is then transferred to a mixer after being metered; saturated steam is firstly transferred to a superheater for heating, then passes through a hot steam drum, and enters the mixer after being metered, so as to be evenly mixed with acetylene gas.

(2) Hydration reaction and catalyst regeneration: the mixed gas is transferred to a boiling-bed hydration reactor, and undergoes a gas-solid phase catalytic reaction by a catalyst in the fluidized bed at a certain temperature and pressure; the reacted gas enters an internal cyclone separator to recover the catalyst, and then passes through an external cyclone separator to capture catalyst powder;

The catalyst consumed due to abrasion must be replenished with fresh catalyst, which is periodically pressed from a catalyst replenishing hopper into the hydration reactor with nitrogen;

The catalyst in the hydration reactor continuously flows into a gas-solid nozzle via the pressure in the reactor, and is continuously transferred to a regenerator with nitrogen for regeneration; the compressed air from an outer tube enters the upper part of the regenerator through an air buffer for heat exchange before entering an air superheater, and then is transferred to the regenerator for regeneration after being heated, so as to burn off coke on the catalyst surface. The exhaust gas after regeneration firstly enters the internal cyclone separator to recover the catalyst particles, then passes through the external cyclone separator to capture the catalyst powder, and finally is vented by a tail gas water seal:

The regenerated catalyst naturally flows into the hydration reactor for further use.

(3) Cooling and separation of reaction gas: the catalyst particles separated and captured reaction gas is cooled and then introduced into a quench column, onto the top of which a dilute acetaldehyde aqueous solution is sprayed by a dilute acetaldehyde pump, while a large amount of soft water is injected through the bottom of the column from a water storage tank to wash and cool the reaction gas; upon cooling the reaction gas, the dilute acetaldehyde is concentrated by heat of the reaction gas. The cooled reaction gas from the top of the quench column enters a water condenser and is condensed with industrial water. The condensate flows into a dilute acetaldehyde intermediate trough, and then enters a dilute acetaldehyde holding tank, and the uncondensed gas enters a brine condenser and is condensed with brine at −5° C., and is separated by a gas-liquid separator; the separated liquid flows into a dilute acetaldehyde holding tank.

(4) Absorption and distillation of acetaldehyde: the uncondensed gas from the gas-liquid separator enters an acetaldehyde absorption column, and water is transferred via a solvent pump to the top of the acetaldehyde absorption column for spraying after being cooled to 5° C. by a water cooler; the absorption liquid is drained through the bottom of the column to the dilute acetaldehyde holding tank. Most of the unabsorbed gas is recycled to the acetylene buffer through a separator and mixed with fresh acetylene as raw material, while the remaining small amount of the unabsorbed gas is vented to prevent affecting the progress of the hydration reaction due to the accumulation of inert gas.

The dilute acetaldehyde from the dilute acetaldehyde holding tank is pumped out by a dilute acetaldehyde feed pump, and then enters an acetaldehyde distillation column for distilling after being preheated by a preheater. The distilled water is returned to the water storage tank for reusing; the acetaldehyde vapor at the top of the column enters an acetaldehyde cooler and is condensed with −5° C. brine: the uncondensed gas is further condensed by the tail gas condenser; the condensate enters the gas-liquid separator for gas-liquid separation; the condensate enters the acetaldehyde intermediate trough, and then enters the acetaldehyde holding tank to obtain acetaldehyde product.

In step (1) of the present application, a molar ratio of water to acetylene n the feed gas ranges from 1 to 6.

In step (2) of the present application, the catalyst used in the hydration reaction is an active metal aluminophosphate molecular sieve type catalyst (ZAPO-5 molecular sieve catalyst) with Zn introduced into the molecular sieve framework structure.

In step (2) of the present application, the pressure in the fluidized bed hydration reactor is 0.5-1 kg/cm$^2$, and the temperature is 290±10° C.

In step (2) of the present application, the temperature for the catalyst regeneration is 500-60° C.

The production process provided by the present application is simple and stable, can reasonably utilize the domestic energy structure in China, and the catalyst used is the currently more maturely studied ZAPO molecular sieve catalyst, which can not only notably reduce production costs and greatly increase production efficiency, but also completely solve the dependence on mercury catalysts in the production of acetaldehyde by acetylene hydration, such that the harm caused by mercury to the human body and the environment can be avoided. Also, by integrating the equipment with the method, the present application facilitates the production and utilization of the operator, and the use of raw materials is also recycled as many times as possible, which can effectively reduce the production cost and save resources at the same time.

DESCRIPTION OF THE DRAWING

FIG. 1 is a process flow diagram for producing acetaldehyde by catalyzing gas phase hydration of acetylene with ZAPO molecular sieve used in the Examples of the present application.

DETAILED DESCRIPTION OF THE INVENTION

The principles and features of the present application are described below, and the enumerated examples are only used for explaining the application, without limiting the scope of the present application.

As shown in FIG. 1. FIG. 1 is a process flow diagram of a preparation method for producing acetaldehyde by catalyzing acetylene with ZAPO molecular sieve and a schematic diagram of some of the equipment. The specific process flow of the present application is as follows:

(1) Preheating and mixing materials: acetylene enters buffer 101 from a gas tank, and is pressurized by water-ring acetylene compressors 102a and 102b before entering a gas-liquid separator 103 to remove moisture therein, and is then transferred to mixer 106 after being metered. Saturated steam is firstly transferred to superheater 104 for heating, then passes through a hot steam drum 105, and enters the mixer 106 after being metered, so as to be evenly mixed with acetylene gas.

(2) Hydration reaction and catalyst regeneration: the mixed gas is transferred to boiling-bed hydration reactor 107, and undergoes a gas-solid phase catalytic reaction by a catalyst in the fluidized bed at a certain temperature and pressure. The reacted gas enters an internal cyclone separator 108 to recover the catalyst, and then passes through an external cyclone separator 109 to capture catalyst powder;

The catalyst consumed due to abrasion must be replenished with fresh catalyst, which is periodically pressed from catalyst replenishing hopper 110 into the hydration reactor 107 with nitrogen.

The catalyst in the hydration reactor 107 continuously flows into a gas-solid nozzle via the pressure in the reactor, and is continuously transferred to regenerator 111 with nitrogen for regeneration. The compressed air from an outer tube enters the upper part of the regenerator through air buffer 112 for heat exchange before entering an air superheater 113, and then is transferred to the regenerator 111 for regeneration after being heated, so as to burn off coke on the catalyst surface. The exhaust gas after regeneration firstly enters internal cyclone separator 114 to recover the catalyst particles, then passes through an external cyclone separator 115 to capture the catalyst powder, and finally is vented by tail gas water seal 116.

The regenerated catalyst naturally flows into the hydration reactor 107 for further use.

(3) Cooling and separation of the reaction gas: the catalyst particles separated and captured reaction gas is cooled and then introduced into quench column 117, onto the top of which a dilute acetaldehyde aqueous solution is sprayed by dilute acetaldehyde pumps 108a and 108b, while a large amount of soft water is injected through the bottom of the column from water storage tank 100 to wash and cool the reaction gas. Upon cooling the reaction gas, the dilute acetaldehyde is concentrated by heat of the reaction gas. The cooled reaction gas from the top of the quench column 117 enters water condensers 119a and 119b, and is condensed with industrial water. The condensate flows into dilute acetaldehyde intermediate trough 120, and then enters dilute acetaldehyde holding tank 121a, and the uncondensed gas enters brine condensers 122a and 122b, and is condensed with brine at −5° C., and is separated by gas-liquid separator 123. The separated liquid flows into the dilute acetaldehyde holding tank 121b.

(4) Absorption and distillation of acetaldehyde: the uncondensed gas from the gas-liquid separator 123 enters acetaldehyde absorption column 124, and water is transferred via solvent pump 125 to the top of the acetaldehyde absorption column 124 for spraying after being cooled to 5° C. by water cooler 126. The absorption liquid is drained through the bottom of the column to the dilute acetaldehyde holding tank 121b. Most of the unabsorbed gas is recycled to the acetylene buffer 101 through separator 127 and mixed with fresh acetylene as raw material, while the remaining small amount of the unabsorbed gas is vented to prevent affecting the progress of the hydration reaction due to the accumulation of inert gas.

The dilute acetaldehyde from the dilute acetaldehyde holding tanks 121a and 121b is pumped out by dilute acetaldehyde feed pumps 128a and 128b, and then enters acetaldehyde distillation column 130 for distilling after being preheated by a preheater 129, The distilled water is returned to the water storage tank 100 for reusing. The acetaldehyde vapor at the top of the column enters acetaldehyde cooler 131 and is condensed with −5° C. brine. The uncondensed gas is further condensed by tail gas condenser 132. The condensate enters gas-liquid separators 133a and 133b for gas-liquid separation. The condensate enters acetaldehyde intermediate troughs 134a and 134b, and then enters acetaldehyde holding tank 135 to obtain acetaldehyde product.

In some embodiments, the present application relates to a preparation method for producing acetaldehyde by catalyzing acetylene with ZAPO molecular sieve, comprising:

Subjecting acetylene after being pressurized to gas-liquid separation to remove moisture, and mixing the same with heated saturated steam to obtain a mixed gas;

Subjecting the mixed gas to a gas-solid phase catalytic reaction by catalyzing with a ZAPO catalyst, and separating and capturing the ZAPO catalyst from the reacted gas to recover the ZAPO catalyst and obtain a reaction gas, and recycling and reusing the ZAPO catalyst after being regenerated;

Spraying the reaction gas after being cooled with a dilute acetaldehyde aqueous solution, and washing and cooling the same with soft water to obtain a cooled reaction gas;

Condensing the cooled reaction gas with water to obtain a condensate and a first uncondensed gas, and condensing the first uncondensed gas with cooled brine to obtain a separated liquid and a second uncondensed gas after gas-liquid separation;

Spraying the second uncondensed gas with cooled water to obtain an absorption liquid and an unabsorbed gas;

Distilling the condensate, the separated liquid and the absorption liquid after being preheated to obtain water and acetaldehyde vapor;

Condensing the acetaldehyde vapor with cooled brine to obtain a third uncondensed gas and an acetaldehyde condensate, and subjecting the acetaldehyde condensate to gas-liquid separation to obtain acetaldehyde.

In some embodiments, a molar ratio of the saturated steam to acetylene ranges from 1 to 6, e.g. from 2 to 4.5. As an example, a space velocity of acetylene can be 10-20 mL/min·mL catalyst, such as 13-16 mL/min·mL catalyst.

In some embodiments, the ZAPO catalyst is a ZAPO-5 molecular sieve catalyst. As an example, a molar ratio $n(Zn):n(P_2O_5)$ of Zn content in the framework of the ZAPO-5 molecular sieve catalyst is 0.3-0.6, but is not limited thereto.

In some embodiments, the gas-solid phase catalytic reaction is performed under the following condition: a pressure of 0.5-1 kg/cm$^2$ and a temperature of 290±10° C.

In some embodiments, the ZAPO catalyst is regenerated at a temperature of 500-600° C.

In some embodiments, the cooled brine is brine at −5° C.

In some embodiments, the cooled water is water at 5° C.

Herein, unless otherwise stated, each number or value representing reaction conditions, parameters, etc. is modified by the term "about" by default. In some embodiments, the term "about" should be understood a variation within ±1% relative to the object that it modifies.

Herein, unless otherwise stated, the terms "comprise", "include" and "contain" or equivalents thereof are open-ended expression, and mean that elements, components and steps that are not specified may be included in addition to those listed.

Herein, unless otherwise stated, singular terms encompass plural referent and vice versa.

Herein, unless otherwise stated, the term "or" is intended to include "and" and vice versa.

All patents, patent applications and other established publications are expressly incorporated herein by reference for the purpose of describing and disclosing. These publications are provided solely because they were disclosed prior to the filing date of the present application. All statements regarding the dates of these documents or the representation of the contents of these documents are based on the information available to the applicant and do not constitute any admission as to the correctness of the dates of these documents or the contents of these documents. Moreover, in any country, any reference to these publications herein does not constitute an admission that the publications form part of the common knowledge in the art.

Unless otherwise stated, the reagents, materials, and devices used in the following Examples and Comparative Examples are all commercially available reagents, materials, and devices known in the art, Unless otherwise stated, the following operations are routine operations known in the art, which, for example, can be seen in the following description: Wang Zhikui et al., "Principle of Chemical Engineering (Fifth Edition)", Chemical Industry Press, January 2018: Huang Xiaorong et at, "Introduction to Fine Chemical industry (Second Edition)", Chemical Industry Press; March 2015; Zhang Chang et at, "Process Principle and Technology of Fine Chemical Industry". Sichuan Science and Technology Press, October 2005.

Example 1

With reference to the process flow shown in FIG. 1, the space velocity of acetylene was 40.5 mL/min-3 mL catalyst, the molar ratio of water to acetylene in the feed gas was 4.5, and the catalyst used in the hydration reaction was ZAPO-5 (zinc aluminophosphate) molecular sieve catalyst, in which the molar ratio $n(Zn):n(P_2O_5)$ for Zn content in the framework was 0.3, and the temperature of the hydration reactor was 290'C, The composition and content of the products obtained in the Example, which was mainly acetaldehyde, were measured by gas chromatography to calculate the conversion rate of acetylene and the selectivity of acetaldehyde.

The measured conversion rate of acetylene was 87.5%, and the selectivity of acetaldehyde was about 98%.

Example 2

With reference to the process flow shown in FIG. 1, the space velocity of acetylene was 15.8 mL/min mL catalyst, the molar ratio of water to acetylene in the feed gas was 2.3, and the catalyst used in the hydration reaction was ZAPO-5 molecular sieve catalyst, in which the molar ratio $n(Zn):n(P_2O_5)$ for Zn content in the framework was 0.4, and the temperature of the hydration reactor was 290° C. The composition and content of the products obtained in the Example, which was mainly acetaldehyde, were measured by gas chromatography to calculate the conversion rate of acetylene and the selectivity of acetaldehyde.

The measured conversion rate of acetylene was 94.2%, and the selectivity of acetaldehyde was about 99%.

Example 3

With reference to the process flow shown in FIG. 1, the space velocity of acetylene was 14.8 mL/min-mL catalyst, the molar ratio of water to acetylene in the feed gas was 2.3, and the catalyst used in the hydration reaction was ZAPO-5 molecular sieve catalyst, in which the molar ratio n(Zn):n (P$_2$O$_5$) for Zn content in the framework was 0.5, and the temperature of the hydration reactor was 290° C. The composition and content of the products obtained in the Example, which was mainly acetaldehyde, were measured by gas chromatography to calculate the conversion rate of acetylene and the selectivity of acetaldehyde.

The measured conversion rate of acetylene was 93.8%, and the selectivity of acetaldehyde was about 99%.

Example 4

With reference to the process flow shown in FIG. 1, the space velocity of acetylene was 15.4 mL/min·mL catalyst, the molar ratio of water to acetylene in the feed gas was 2.2, and the catalyst used in the hydration reaction was ZAPO-5 molecular sieve catalyst, in which the molar ratio n(Zn):n (P$_2$O$_5$) for Zn content in the framework was 0.6, and the temperature of the hydration reactor was 290° C. The composition and content of the products obtained in the Example, which was mainly acetaldehyde, were measured by gas chromatography to calculate the conversion rate of acetylene and the selectivity of acetaldehyde.

The measured conversion rate of acetylene was 93.5%, and the selectivity of acetaldehyde was about 99%.

The selectivities of acetaldehyde prepared by the process of Examples 1-4 are all 98% or more, and the conversion rates of raw material acetylene are 87.5% or more. It can be seen that the yield of acetaldehyde prepared by the method of the present application is extremely high, and the conversion rate of raw materials is also quite good, Compared with the traditional method, the method of the present application has higher yield and less pollution to the environment. Also, the catalyst has been recycled and reused for multiple times, and the undissolved acetaldehyde raw material has also been recycled and reused, which effectively save costs. The present application does not use the mercury catalyst in the traditional method, which effectively avoids the impact on operators/production environment, has high promotion value and commercial value, and is suitable for production use.

The above description shows and describes several preferred examples of the present invention. However, as mentioned above, it should be understood that the present application is not limited to the form disclosed herein, and should not be regarded as an exclusion of other embodiments, but can be used in various other combinations, modifications, and environments, and can be changed within the scope of the inventive concept described herein through the above teachings or the technology or knowledge in related art. Without departing from the spirit and scope of the present application, the modifications and changes made by those skilled in the art should fall within the protection scope of the appended claims of the present application.

What is claimed is:
1. A preparation method for continuously producing acetaldehyde by catalyzing gas phase hydration of acetylene with ZAPO molecular sieve, comprising:
(1) allowing acetylene to enter a buffer from a gas tank, and to be pressurized by a water-ring acetylene compressor before entering a gas-liquid separator to remove moisture therein, and then transferring the same to a mixer after being metered; transferring saturated steam to a superheater for heating, then passing it through a hot steam drum, and allowing it to enter the mixer after being metered, so as to be evenly mixed with acetylene gas to obtain a mixed gas;
(2) transferring the mixed gas to fluidized bed hydration reactor, and subjecting it to a gas-solid phase catalytic hydration reaction by a catalyst in the fluidized bed hydration reactor at a certain temperature and pressure, to obtain a reaction gas;
(3) after the hydration reaction, cooling and then introducing the reaction gas into a quench column, onto the top of which a dilute acetaldehyde aqueous solution is sprayed by a dilute acetaldehyde pump, while injecting a large amount of soft water through the bottom of the column from a water storage tank to wash and cool the reaction gas; upon cooling the reaction gas, concentrating the dilute acetaldehyde by heat of the reaction gas; allowing the cooled reaction gas from the top of the quench column to enter a water condenser and to be condensed with industrial water, to obtain a condensate and an uncondensed gas; allowing the condensate to flow into a dilute acetaldehyde intermediate trough, and then enter a dilute acetaldehyde holding tank, and allowing the uncondensed gas to enter a brine condenser to be condensed, and to be separated by a gas-liquid separator; allowing the separated liquid to flow into a dilute acetaldehyde holding tank;
(4) allowing the uncondensed gas from the gas-liquid separator to enter an acetaldehyde absorption column, and transferring water via a solvent pump to the top of the acetaldehyde absorption column for spraying after being cooled to 5° C. by a water cooler, to obtain an absorption liquid and an unabsorbed gas; draining the absorption liquid through the bottom of the column to the dilute acetaldehyde holding tank; pumping out the dilute acetaldehyde from the dilute acetaldehyde holding tank by a dilute acetaldehyde feed pump, and then allowing it to enter an acetaldehyde distillation column for distilling after being preheated by a preheater, to obtain a distilled water and an acetaldehyde vapor; returning the distilled water to the water storage tank for reusing; allowing the acetaldehyde vapor at the top of the column to enter an acetaldehyde cooler and to be condensed, to obtain an uncondensed gas and a condensate; further condensing the uncondensed gas by a tail gas condenser; allowing the condensate to enter the gas-liquid separator for gas-liquid separation; allowing the condensate after gas-liquid separation enter the acetaldehyde intermediate trough, and then enter the acetaldehyde holding tank to obtain acetaldehyde product.

2. The preparation method according to claim 1, wherein, in step (1), a molar ratio of the saturated steam to acetylene ranges from 1 to 6.

3. The preparation method according to claim 1, wherein, in step (2), the catalyst used in the hydration reaction is an active metal aluminophosphate molecular sieve type catalyst with Zn introduced into the molecular sieve framework structure.

4. The preparation method according to claim 1, wherein, in step (2), the pressure in the fluidized bed hydration reactor is 0.5-1 kg/cm$^2$, and the temperature is 290±10° C.

5. The preparation method according to claim 1, wherein, step (2) also comprises a catalyst regeneration process as follows,
the reaction gas after the hydration reaction flows into an internal cyclone separator to recover the catalyst, and then passes through an external cyclone separator to capture catalyst powder; the catalyst consumed due to abrasion is replenished with fresh catalyst, which is periodically pressed from a catalyst replenishing hopper into the hydration reactor with nitrogen; the catalyst in the hydration reactor continuously flows into a gas-solid nozzle via the pressure in the reactor, and is continuously transferred to a regenerator with nitrogen for regeneration; compressed air from an outer tube enters the upper part of the regenerator through an air buffer for heat exchange before entering an air superheater, and then is transferred to the regenerator for regeneration after being heated, so as to burn off coke on the catalyst surface; the exhaust gas after regeneration firstly enters an internal cyclone separator to recover catalyst particles, then passes through an external cyclone separator to capture catalyst powder, and finally is vented by a tail gas water seal; the regenerated catalyst naturally flows into the hydration reactor for further use.

6. The preparation method according to claim 5, wherein, a temperature of catalyst regeneration is 500-600° C.

7. The preparation method for according to claim 1, wherein, step (4) further includes the operation of recovering the unabsorbed gas as follows: most of the unabsorbed gas is recycled to the acetylene buffer through a separator and is mixed with fresh acetylene as a raw material, and the remaining small amount of the unabsorbed gas is vented.

8. The preparation method according to 1, wherein, the condensation conditions in steps (3) and (4) are condensed by brine of −5° C.

9. A preparation method for producing acetaldehyde by catalyzing acetylene with ZAPO molecular sieve, comprising:
subjecting acetylene after being pressurized to gas-liquid separation to remove moisture, and mixing the same with heated saturated steam to obtain a mixed gas;
subjecting the mixed gas to a gas-solid phase catalytic reaction by catalyzing with a ZAPO catalyst, and separating and capturing the ZAPO catalyst from the reacted gas to recover the ZAPO catalyst and obtain a reaction gas, and recycling and reusing the ZAPO catalyst after being regenerated;
spraying the reaction gas after being cooled with a dilute acetaldehyde aqueous solution, and washing and cooling the same with soft water to obtain a cooled reaction gas;
condensing the cooled reaction gas with water to obtain a condensate and a first uncondensed gas, and condensing the first uncondensed gas with cooled brine to obtain a separated liquid and a second uncondensed gas after gas-liquid separation;
spraying the second uncondensed gas with cooled water to obtain an absorption liquid and an unabsorbed gas;
distilling the condensate, the separated liquid and the absorption liquid after being preheated to obtain water and acetaldehyde vapor;
condensing the acetaldehyde vapor with cooled brine to obtain a third uncondensed gas and an acetaldehyde condensate, and subjecting the acetaldehyde condensate to gas-liquid separation to obtain acetaldehyde.

10. The method according to claim 9, wherein a molar ratio of the saturated steam to acetylene ranges from 1 to 6.

11. The method according to claim 9, wherein the ZAPO catalyst is a ZAPO-5 molecular sieve catalyst.

12. The method according to claim 9, wherein the gas-solid phase catalytic reaction is performed under the following condition: a pressure of 0.5-1 kg/cm$^2$ and a temperature of 290±10° C.

13. The method according to claim 9, wherein the ZAPO catalyst is regenerated at a temperature of 500-600° C.

14. The method according to claim 9, wherein the cooled brine is brine at −5° C.

15. The method according to claim 9, wherein the cooled water is water at 5° C.

* * * * *